United States Patent [19]

Mimoun et al.

[11] Patent Number: 5,580,996
[45] Date of Patent: Dec. 3, 1996

[54] OXYGEN-CONTAINING ALIPHATIC COMPOUNDS AND THEIR USE AS INTERMEDIATES FOR THE PREPARATION OF 4-HYDROXY-2, 5-DIMETHYL-3(2H)-FURANONE

[75] Inventors: Hubert Mimoun, Challex, France; Alexander Zaslona, Geneva; Jean-Paul Leresche, Preverenges, both of Switzerland

[73] Assignee: Firmenich SA, Geneva, Switzerland

[21] Appl. No.: 416,809

[22] PCT Filed: Sep. 1, 1994

[86] PCT No.: PCT/IB94/00261

§ 371 Date: Apr. 13, 1995

§ 102(e) Date: Apr. 13, 1995

[87] PCT Pub. No.: WO95/07876

PCT Pub. Date: Mar. 23, 1995

[30] Foreign Application Priority Data

Sep. 14, 1993 [CH] Switzerland .............................. 2755/93

[51] Int. Cl.⁶ .................................................. C07D 303/14
[52] U.S. Cl. ........................... 549/477; 568/385; 568/405; 568/413; 568/673
[58] Field of Search ..................... 568/673, 413, 568/477, 385, 405, 413, 873; 549/477

[56] References Cited

U.S. PATENT DOCUMENTS

| | | | |
|---|---|---|---|
| 3,576,014 | 4/1971 | Meyrin et al. | 549/477 |
| 3,728,397 | 4/1973 | Re et al. | 568/413 |
| 3,853,916 | 12/1974 | van den Ouweland | 549/477 |
| 4,290,960 | 9/1981 | Ross et al. | 549/477 |
| 4,464,409 | 8/1984 | de Rooij | 549/477 |

FOREIGN PATENT DOCUMENTS

| | | | |
|---|---|---|---|
| 474500 | 8/1969 | France | 508/385 |

OTHER PUBLICATIONS

Harsh Gopal et al. "Ruthenium Tetroxide Oxidation of Alkynes. A New One Step Synthesis of Alpha–Kiketones"; Tetrahedron Letters No. 31, Juillet 1971, Oxford GB, pp. 2941–2944.

Eugen Müller, "Methoden der Organischen Chemie (Houben–Weyl)" Band V1/2, Sauerstoffverbindungen 1, 1965; pp. 19–20.

*Primary Examiner*—James H. Reamer
*Attorney, Agent, or Firm*—Pennie & Edmonds

[57] ABSTRACT

The compounds of the invention are characterised by the formulae

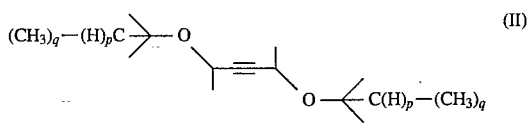

and

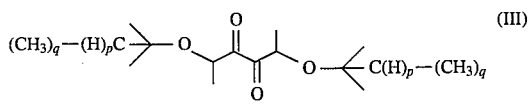

wherein index p represents an integer equal to 2 or 3 and q can take the value zero or 1, with the provision that p+q=3. Said compounds are obtained from hex-3-yne-2,5-diol following a process which comprises reacting an ethylenic compound of formula $$(CH_3)_2C=C(H)_n(CH_3)_m \qquad (I)$$

wherein index n represents an integer equal to 1 or 2 and m can take the values zero or 1 and wherein n+m=2, with hex-3-yne-2,5-diol, followed by the oxidation of the acetylenic ether obtained by means of ruthenium tetroxide. The compounds of formula (III) can be used as intermediate products for the preparation of 4-hydroxy-2,5-dimethyl-3(2H)-furanone (Furaneol®).

11 Claims, No Drawings

OXYGEN-CONTAINING ALIPHATIC COMPOUNDS AND THEIR USE AS INTERMEDIATES FOR THE PREPARATION OF 4-HYDROXY-2, 5-DIMETHYL-3(2H)-FURANONE

TECHNICAL FIELD AND PRIOR ART

This appln is a 371 of PCT/IB94/00261, Sep. 01,1994.

4-Hydroxy-2,5-dimethyl-3(2H)-furanone, a compound better known under its commercial tradename of Furaneol® [registered trademark of Firmenich SA, Geneva], is an essential component of the pineapple and strawberry aromas and, in this capacity, it is widely used in the flavor industry. As a result of its organoleptic properties, it has found extensive use in a wide number of flavoring compositions, wherein it enhances the fruity and caramel note characteristic of the above-mentioned fruits.

Since its discovery, there have been suggested quite a number of methods for its preparation, amongst which it is fitting to cite the synthesis which resorts to the use of hex-3-yne-2,5-diol as a starting product [see Swiss patent no 474'500]. This process can be thus represented:

Scheme

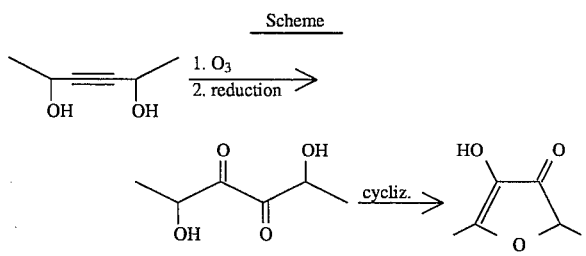

Although this type of process is quite satisfactory from an industrial point of view, it is nevertheless defined by critical steps which require specific industrial facilities and meticulous handling. Thus, it is not surprising to observe that many research teams have been looking into this problem. However, no valid alternative has been able to impose itself up until now.

DESCRIPTION OF THE INVENTION

The present invention is intended to bring a novel solution. More particularly, it relates to oxygen-containing aliphatic compounds which can be used as intermediate products for the preparation of Furaneol®. The compounds in question here are the di-tert-butyl and diisoamyl esters of hex-3-yne-2,5-diol, or 2,5-di-tert-butyloxy-hex-3-yne and 2,5-diisoamyloxy-hex-3-yne, as well as 2,5-di-tert-butyloxy-hexane-3,4-dione and 2,5-diiosamyloxy-hexane-3,4-dione. These are novel compounds which are obtained by an original process which is also the object of the present invention, which process is characterised in that a. hex-3-yne-2,5-diol is reacted with an ethylenic compound of formula $(CH_3)_2C=C(H)_n(CH_3)_m$  (I)

wherein index n represents an integer equal to 1 or 2 and q can take the values of zero or 1 and wherein n+m=2, to form an acetylenic ether of formula

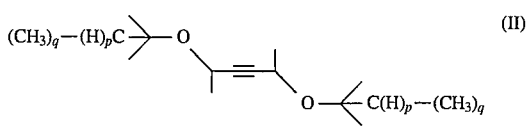

wherein index p represents an integer equal to 2 or 3 and q can be zero or 1 and wherein p+q=3; and b. said acetylenic ether is oxidised by means of catalytic amounts of ruthenium tetroxide, in the presence of an agent capable of re-oxidising the formed $RuO_2$, to provide the corresponding hexane-3,4-dione of formula

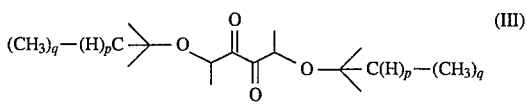

wherein indexes p and q have the meaning indicated above.

Hex-3-yne-2,5-diol, used as starting product in the process of the invention, is a commercially available product. As the ethylenic reagent of formula (I), there is used isobutene (n=2; m=0) or 2-methyl-but-2-ene (n=m=1). The latter can be replaced by isoamylene, a mixture containing predominant amounts of 2-methyl-but-2-ene together with its isomer 2-methyl-but-1-ene.

This first step of the process of the invention, which formally consists in the etherification of the hexyne-diol, is preferably carried out in anhydrous medium and at a temperature below 80° C., and preferably comprised between 0° and 40° C. The reaction can be carried out continuously, or batchwise in an autoclave.

Since hex-3-yne-2,5-diol is viscous at low temperature, it is more convenient to operate in the presence of a solvent, which also allows better control of the reaction's exothermicity. To this end, ethers such as methyl-tertbutyl ether or diisopropyl ether are particularly convenient. Aromatic solvents such as toluene can also be used.

In this way, the 2,5-di-tert-butyloxy- or 2,5-diisoamyloxy-hex-3-yne obtained in organic solution can be directly employed in the following step of the process, without separation or subsequent purification.

The etherification reaction is also favored by the action of an anhydrous acidic catalyst. This can be a protonic acid, for example p-toluenesulfonic acid, a Lewis-type acid such as $BF_3.Et_2$, or yet an acid resin such as the sulfonic resins. The particular choice amongst these reagents will be made on the basis of economic considerations, availability of the reagent and protection of the environment. In this manner, we obtained particularly high, close to quantitative, yields.

The second step of the process is characterised by the oxidation of the acetylenic ether thus obtained, which oxidation is carried out by means of $RuO_4$, or of any $RuO_4$ precursor which is capable of generating the latter under the reaction conditions, said $RuO_4$ being used in catalytic amounts. Thus operated, the reaction requires the presence of an agent able to re-oxidise the formed $RuO_2$.

This type of oxidation is known per se.

Whether in combination with sodium hypochlorite, with periodates or yet with organic peracids, $RuO_4$ has been used to promote a number of oxidations of various substrates. Gopal and Gordon have shown [Tetr. Lett. 1971, 31, 2941] that the $NaOCl/RuO_4$ system was particularly well-adapted to the conversion of alcynes into α-diketones. This type of oxidation, which is applied here for the first time to substrates such as those represented by the formula (II) ethers, provides good yields in the corresponding dione and is particularly convenient for the preparation of compounds (III) of the invention.

According to a current method, the required initial formation of $RuO_4$ can be obtained by reacting $RuCl_3$ with the oxidising agent, for example a solution of NaOCl. The proportion of starting $RuCl_3$ can vary in a wide range of values comprised between about 0.1 and 0.2% molar, relative to the starting acetylenic ether. The reaction is pursued until complete conversion of the latter, using the required amount of hypochlorite. This amount is of the order of four equivalents relative to the acetylenic ether.

The oxidation takes place by dissolving the reagents in an inert organic solvent. Such solvents are selected amongst the chlorinated solvents, namely $CH_2Cl_{12}$ or $CCl_{14}$, or ethers such as diisopropyl ether or methyl-tertbutyl ether, or even the aromatic solvents such as toluene.

The degree of acidity of the reaction medium also plays a role in obtaining good yields in the final product. We observed that the best yields were obtained when operating at pH values comprised between 5 and 9.

As indicated above, the novel compounds of the invention are useful as intermediate products for the preparation of Furaneol®. In fact, the ether diones (III) can be cyclized, under the action of acidic cyclizing agents, to form 4-hydroxy-2,5-dimethyl-3(2H)-furanone. We have been able to establish that, by applying the process of the invention, the latter could be obtained in excellent yields, that the formation of side-products could be avoided, which formation is undesirable both from the point of view of their organoleptic effect on the final product and from the point of view of their elimination, and that having to resort to the use of specific and complex installations could at last be avoided. Therefore, such a process provides an undeniable improvement over the processes known heretofore. Alternatively, the ketonic ethers of formula (III) according to the invention can be obtained via ozonolysis of the acetylenic ethers of formula (II), following a process similar to the methods known per se.

Embodiments of the invention

The invention will be described in detail by way of the following examples wherein the temperatures are indicated in degrees centigrade.

EXAMPLE 1

2,5-Di-tert-butyloxy-hex-3-yne

A mixture of 290 g (2.54 mole) of hex-3-yne-2,5-diol, 150 g of methyl-tert-butyl ether (MTBE) and 75 g of sulfonic resin [Amberlite®, A 15] was kept under stirring and heated to 70° so as to eliminate any water present by means of a separator.

The mixture was then cooled to room temperature and, after replacing the separator with a condenser, 100 g (1.78 mole) of isobutylene were introduced. After a quick decrease to 0°/–3°, the temperature goes up to 30°. Another fraction of 100 g of isobutylene was added to the mixture and the operation was thus repeated until a total amount of isobutylene equal to 8 moles [450 g; addition time: 5h] had been reached. The solution obtained is filtered and the resin present is recovered for subsequent use. The solution was thus ready for the following oxidation step.

When operating as indicated above, but replacing the isobutylene with a mixture of isoamylene (85% of 2-methyl-but-2-ene- 15% of 2-methyl-but-1ene), there was obtained 2,5-diisoamyloxy-hex-3-yne. SM:z/e: 97, 43, 71, 79.

EXAMPLE 2

2,5-Di-tert-butyloxy-hexane-3,4-dione

A mixture consisting of 60 g of 2,5-di-tert-butyloxy-hex-3-yne (0.265 mole), 60 g of methyl-tert-butyl ether (MTBE) and 200 g of water was kept at 40° under vigorous stirring, in the presence of 0.1 g of $RuCl_3$. The pH, which was about 2.3, was brought to 7 with a 30% aqueous solution of NaOH and a 15% aqueous solution of $H_3PO_4$.

600 g (4 equiv.) of a 13.4% aqueous solution of NaOCl were then added to the reaction mixture, while maintaining the pH at about 7 by automatic introduction of a 15% aqueous solution of phosphoric acid. The reaction evolution was followed by gas chromatography analysis.

Once complete conversion had been reached, the mixture was cooled to 25° and decanted, then the organic phase was washed with 100 g of water and the $RuO_4$ was separated by decantation. After evaporating the MTBE present, 2,5-di-tert-butyloxy-hexane-3,4-dione was recovered with a purity above 99% and in 78% yield.

Similar results were obtained when replacing NaOCl with peracetic acid. The latter is preferably obtained through extraction of aqueous peracetic acid with isopropyl acetate. The reaction is then carried out in the presence of N-methylpyrrolidone.

The compound thus obtained was then used for the preparation of 4-hydroxy-2,5-dimethyl-3(2H)-furanone via cyclization by means of an acidic cyclization agent.

EXAMPLE 3

2,5-Di-tert-butyl oxy-hexane-3,4-dione 113 g of 2,5-di-tert-butyloxy-hex-3-yne, obtained as described in Example 1, and 10 g of decaline in 280 g of methanol were placed in a bath kept at −30° with a thermostat, then an ozone flow at 100 l/h was introduced. After the starting product had completely vanished (6 h), degassing was carried out by passing a slight air flow during 15 min, and 46 g of dimethyl sulfide were added over a period of 1.5 h.

The resulting solution is kept at rest for one night and then concentrated. 126 G of the desired dione were thus obtained.

We claim:

1. Acetylenic ethers of formula $$(CH_3)_q-(H)_pC \!\!>\!\!-O-C(CH_3)=C(CH_3)-O-\!\!<\!\!C(H)_p-(CH_3)_q \quad (II)$$

wherein index p represents an integer equal to 2 or 3 and q can take the value zero or 1 and wherein p+q=3.

2. Ketonic ethers of formula $$(CH_3)_q-(H)_pC \!\!>\!\!-O-C(CH_3)(O)-C(CH_3)(O)-O-\!\!<\!\!C(H)_p-(CH_3)_q \quad (III)$$

wherein index p represents an integer equal to 2 or 3 and q can take the value zero or 1 and wherein p+q=3.

3. Process for the preparation of ethers comprising the steps of:

reacting sufficient amounts of hex-3-yne-2,5-diol with an ethylenic compound of formula $$(CH_3)_2C=C(H)_n(CH_3)_m \quad (I)$$

wherein index n represents an integer equal to 1 or 2 and m can take the values zero or 1 and wherein n+m=2, to provide an acetylenic ether of formula

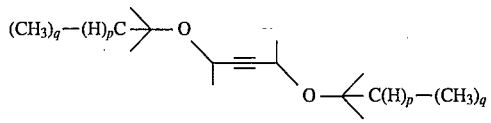

and oxidizing said acetylenic ether in the presence of catalytic amounts of ruthenium tetroxide and an agent capable of re-oxidizing $RuO_2$ to form a ketonic ether of formula

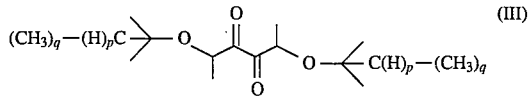

wherein index p represents an integer equal to 2 to 3 and q can take the value zero or 1, with the provision that p+q=3.

4. Process according to claim 3 a., characterized in that the reaction is carried out in anhydrous medium and at a temperature below 80° C.

5. Process according to claim 3, characterized in that the oxidation is carried out in the presence of $NaOCl/RuO_4$.

6. Process according to claim 3, characterized in that the oxidation is carried out in the presence of an organic peracid/$RuO_4$.

7. Process according to claim 5, characterized in that the required catalytic amount of $RuO_4$ is obtained in situ by reaction of NaOCl on $RuCl_3$ and in that the latter is used in a proportion comprised between about 0.1 and 0.2% molar relative to the starting acetylenic ether.

8. Process according to claim 7, characterized in that NaOCl is used in a proportion of about 4 equivalents relative to the starting acetylenic ether.

9. Process according to claim 3, characterized in that the oxidation is carried out either in a chlorinated solvent or in an ether.

10. Process according to claim 3, characterized in that the oxidation is carried out in the presence of methyl-tert-butyl ether.

11. A method for the preparation of 4-hydroxy-2,5-dimethyl-3(2H)-furanone which comprises cyclizing the ether of claim 2 under suitable process conditions to form said 4-hydroxy-2,5-dimethyl-3(2H)-furanone.

* * * * *